（12） United States Patent
Liu et al.

(10) Patent No.: US 11,490,641 B2
(45) Date of Patent: Nov. 8, 2022

(54) DETECTION OF MULTI-DIMENSIONAL HEATING PATTERNS IN THERMAL FOOD PROCESSES USING THERMOCHROMIC INKS

(71) Applicant: Campbell Soup Company, Camden, NJ (US)

(72) Inventors: Hua Liu, Moorestown, NJ (US); Mark Robert Watts, Marlton, NJ (US)

(73) Assignee: Campbell Soup Company, Camden, NJ (US)

( * ) Notice: Subject to any disclaimer, the term of this patent is extended or adjusted under 35 U.S.C. 154(b) by 846 days.

(21) Appl. No.: 16/414,159

(22) Filed: May 16, 2019

(65) Prior Publication Data

US 2019/0350231 A1 Nov. 21, 2019

Related U.S. Application Data

(60) Provisional application No. 62/672,821, filed on May 17, 2018.

(51) Int. Cl.
*G01N 21/78* (2006.01)
*A23L 3/04* (2006.01)
(Continued)

(52) U.S. Cl.
CPC .................. *A23L 3/04* (2013.01); *A23L 3/32* (2013.01); *A23L 3/3418* (2013.01); *G01N 21/78* (2013.01);
(Continued)

(58) Field of Classification Search
CPC . A23L 3/04; A23L 3/32; A23L 3/3418; A23L 3/01; A23L 3/26; G01N 21/78;
(Continued)

(56) References Cited

U.S. PATENT DOCUMENTS 6,866,863 B2 3/2005 Ribi
2002/0034475 A1 3/2002 Ribi
(Continued)

FOREIGN PATENT DOCUMENTS

JP 2003315167 11/2003
WO WO-2007016131 A1 * 2/2007 ......... B65D 81/3453
(Continued)

OTHER PUBLICATIONS

"International Search Report and Written Opinion," for PCT Application No. PCT/US2019/032807 dated Sep. 6, 2019 (14 pages).
(Continued)

*Primary Examiner* — Abdullahi Nur
(74) *Attorney, Agent, or Firm* — Pauly, DeVries Smith & Deffner LLC

(57) ABSTRACT

Embodiments herein relate to articles and methods for detecting heating patterns within model food compositions containing irreversible thermochromic ink, and for creating multi-dimensional temperature distribution profiles within a packaged model food composition. In an embodiment, a packaged model food composition for thermal testing is included. The packaged model food composition can include a package and a model food composition disposed in the package. The model food composition can include a model food material that shares processing characteristics with a target food material and 0.05 wt. % to 20 wt. % of one or more irreversible thermochromic inks. The irreversible thermochromic inks can exhibit a variable change in at least one color parameter in response to temperature change across a selected temperature range. Other embodiments are also included herein.

20 Claims, 14 Drawing Sheets

(51) Int. Cl.
*A23L 3/32* (2006.01)
*A23L 3/3418* (2006.01)
*G01N 21/84* (2006.01)
*G01N 25/02* (2006.01)
*G01N 33/02* (2006.01)

(52) U.S. Cl.
CPC ............. *G01N 21/84* (2013.01); *G01N 25/02* (2013.01); *G01N 33/02* (2013.01); *G01N 2021/8472* (2013.01)

(58) Field of Classification Search
CPC ........ G01N 21/84; G01N 25/02; G01N 33/02; G01N 2021/8472
See application file for complete search history.

(56) References Cited

U.S. PATENT DOCUMENTS

| | | | |
|---|---|---|---|
| 2009/0226576 | A1 | 9/2009 | Kanehara et al. |
| 2012/0241443 | A1 | 9/2012 | Tang et al. |
| 2016/0200930 | A1 | 7/2016 | Ribi |

FOREIGN PATENT DOCUMENTS

| | | |
|---|---|---|
| WO | 2017203851 | 11/2017 |
| WO | 2017218655 | 12/2017 |
| WO | 2019222588 | 11/2019 |

OTHER PUBLICATIONS

Peng, Jing et al., "Microwave Pasteurization of pre-packaged carrots," Journal of Food Engineering 202(2017) 56-64 (9 pages).
"Technical Product Information," Kromagen Magenta MB50Y-NH, TMCHallcrest, Feb. 11, 2015, sheets 1-7, URL: <http://www.tmchallcrest.com/pdfs/lnk/IN-Kromagen%20magenta%20MB50Y%20NH%20%20MB%2060%20Nh%20K65%20NH%20Concentrate%20Screen%20&%20Flexo-TDS.pdf> (7 pages).
Wang, J. et al., "A New Chemical Marker-Model Food System for Heating Pattern Determination of Microwave-Assisted Pasteurization Processes," Food and Bioprocess Technology, 2018, vol. 11, pp. 1274-1285 (12 pages).
Zhang, Wenjia et al., "Chemical marker M2 (4-hydroxy-5-methyl-3(2H)-furanone) formation in egg white gel model for heating pattern determination of microwave-assisted pasteurization processing," Journal of Food Engineering 125 (2014) 69-76 (8 pages).
Lau, M. H. et al., "Kinetics of Chemical Marker Formation in Whey Protein Gels for Studying Microwave Sterilization," Journal of Food Engineering 60 (2003), 397-405 (9 pages).
Pandit, R. B. et al., "Development of a Novel Approach to Determine Heating Pattern Using Computer Vision and Chemical Marker (M-2) Yield," Journal of Food Engineering 78 (2007) 522-528 (7 pages).
Pandit, R. B. et al., "Kinetics of Chemical Marker M-2 Formation in Mashed Potato- A Tool to Locate Cold Spots Under Microwave Sterilization," Journal of Food Engineering 76 (2006) 353-361 (9 pages).
Pandit, Ram B. et al., "A Computer Vision Method to Locate Cold Spots in foods in Microwave Sterilization Processes," Pattern Recognition 40 (2007) 3667-3676 (10 pages).
"Product Data Sheet—Permanent Thermochromic Change Pigments & Coatings," PDS078 Rev00, LCR Hallcrest LLC, available as early as Apr. 19, 2018 (1 page).
"Safety Data Sheet—Irreversible Chromatic Ink—NH," MSDS004 Revision 4, LCR Hallcrest LLC, revised May 27, 2015 (4 pages).
Tang, Zhongwei et al., "Microwave Sterilization of Sliced Beef in Gravy in 7-oz Trays," Journal of Food Engineering 89 (2008) 375-383 (9 pages).
Wang, Yu et al., "Using Whey Protein Gel as a Model Food to Study Dielectric Heating Properties of Salmon (*Oncorhynchus gorbuscha*) Fillets," LWT—Food Science and Technology 42 (2009) 1174-1178 (5 pages).

* cited by examiner

DETECTION OF MULTI-DIMENSIONAL HEATING PATTERNS IN THERMAL FOOD PROCESSES USING THERMOCHROMIC INKS

This application claims the benefit of U.S. Provisional Application No. 62/672,821, filed May 17, 2018, the content of which is herein incorporated by reference in its entirety.

FIELD

Embodiments herein relate to detecting heating patterns within model food compositions. More specifically, embodiments herein relate to articles and methods for detecting heating patterns within model food compositions containing irreversible thermochromic ink, and for creating multi-dimensional temperature distribution profiles within a packaged model food composition.

BACKGROUND

Thermal processing of packaged food products combines heat and/or pressure with exposure time to eliminate food-borne pathogenic microorganisms. Conventional thermal food processing technologies, such as retort processing, generally involve filling food processing containers with a foodstuff, sealing the food processing container, and then exposing the packaged foods to heated steam under high pressure. In these conventional systems, the food products are heated primarily through conduction of heat energy There is a need for the elimination of food-borne pathogenic microorganisms to be highly consistent to ensure food safety. Determining heating patterns with a packaged food allows for effective design of a thermal process as well as monitoring of the process. Conventional methods for determining heating patterns within a packaged food product during retort processing include the use of thermal sensors such as thermocouples inside the food packages.

Sterilization/pasteurization techniques using electromagnetic waves and/or pressure represent newer approaches for eliminating pathogenic microorganisms within packaged food products. In some of these new systems, the food products are heated, at least partially, through the absorption of the electromagnetic waves by the food material.

SUMMARY

Embodiments herein relate to articles and methods for detecting heating patterns within model food compositions containing irreversible thermochromic ink, and for creating multi-dimensional temperature distribution profiles within a packaged model food composition. In an embodiment, a packaged model food composition for thermal testing is included. The packaged model food composition can include a package and a model food composition disposed in the package. The model food composition can include a model food material that shares processing characteristics with a target food material and 0.05 wt. % to 20 wt. % of one or more irreversible thermochromic inks. The irreversible thermochromic inks can exhibit a variable change in at least one color parameter in response to temperature change across a selected temperature range.

In an embodiment, a method of processing a packaged model food composition is included herein. The method can include creating a model food composition by mixing a model food material and 0.05 wt. % to 20 wt. % of one or more irreversible thermochromic inks. One or more irreversible thermochromic inks can exhibit a variable change in more than one color parameter in response to temperature change across a selected temperature range. The method can also include packaging the model food composition by filling a food processing container with the model food composition and sealing the food processing container. The method can also include processing the packaged model food composition in a thermal process.

In an embodiment, a method for detecting a heating pattern within a packaged model food composition is included. The method can include processing a packaged model food composition using a thermal process across a selected temperature range, the model food composition comprising a model food material and 0.05 wt. % to 20 wt. % of one or more irreversible thermochromic inks. One or more irreversible thermochromic inks exhibit a variable change in more than one color parameter in response to temperature change across the selected temperature range. The method can include recording more than one change in a color parameter of the one or more irreversible thermochromic inks within the processed model food composition. The method can also include assembling a multi-dimensional (such as 2 or 3-dimensional) heating pattern within the processed model food composition using the recorded color parameter changes.

In an embodiment, a method for detecting a high-resolution temperature distribution within a packaged model food composition is included. The method can include processing a packaged model food composition using a thermal process across a selected temperature range, the model food composition comprising a model food material and 0.05 wt. % to 20 wt. % of one or more irreversible thermochromic inks. One or more of the irreversible thermochromic inks can exhibit a variable change in more than one color parameter in response to temperature change across the selected temperature range. The method can include sectioning the processed model food composition into a plurality of sections, each in an x direction, a y direction, or a z direction. The method can also include recording images at a plurality of locations within each of the plurality of sections using an imaging device to obtain a color measurement containing one or more color parameters unique to each of the plurality of locations. The method can also include correlating each unique color measurement at each of the plurality of locations with a corresponding specific temperature using a standard temperature color curve. The method can also include assembling a 3-dimentional temperature distribution profile within the processed model food composition.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
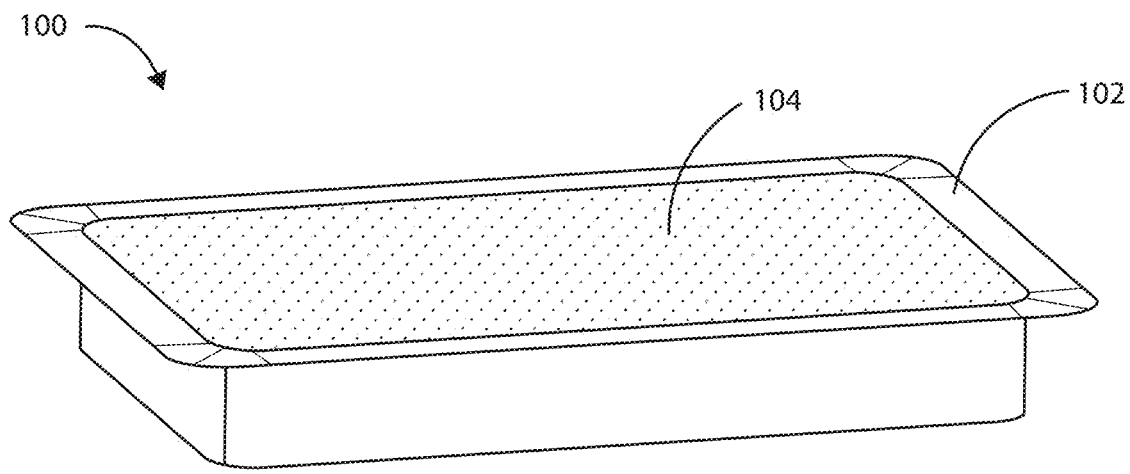
FIG. 1 is a schematic perspective view of a packaged model food composition in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Electromagnetic wave-based sterilization/pasteurization techniques, such as microwave and/or radiofrequency systems, represent newer approaches for eliminating pathogenic microorganisms within packaged food products. In these new systems, the food products are heated, at least partially, through the absorption of the electromagnetic waves by the food material. However, there is a need to ensure the consistency of the thermal processing provided by electromagnetic wave-based sterilization/pasteurization techniques. There can also a need to map the heating pattern within food packages in three-dimensions. There can also a need to identify the cold spot(s) within packages as defined by the X, Y, and Z axis position(s) of the cold spot(s) within the package.

Embodiments herein relate to detecting heating patterns within model food compositions. In some embodiments, the methods for detecting heating patterns within model food compositions can employ an irreversible thermochromic ink for use in creating three-dimensional temperature distribution profiles within a packaged model food composition. The heating patterns determined using model food compositions can be translated to the behavior of a target food composition under similar processing conditions.

High-temperature activated irreversible thermochromic inks can be utilized to detect heating patterns within a model food composition treated by a thermal process. Thermal processes herein can include any process which results in the transfer of heat into a composition wherein the resulting elevation of temperature causes complete or partial inactivation or destruction of microbes therein. Heat can be transferred into a food composition using one or more of conduction, convection, and radiation. In some cases, irreversible thermochromic inks can be activated at a range of temperatures suitable for use with electromagnetic wave-based thermal processes such as microwave-based and/or radio wave-based approaches and/or pressure-based approaches. High-temperature activated irreversible thermochromic inks change color in response to a change from a ground state, which can be clear or white, to an excited state, which can be colored. The change in color from a ground to an excited state can occur at a temperature within the range of temperatures suitable for a thermal process for packaging model food compositions. Irreversible thermochromic ink is irreversible in the sense that it does not change in color upon cooling to lower than thermal processing temperatures.

Irreversible thermochromic inks can be used within model food compositions to create three-dimensional temperature distribution maps within the model food composition in response to a thermal process. The one or more specifically chosen irreversible thermochromic inks and the model food system can be optimized to allow the largest possible color gradient contrast so that heating patterns and cold spot locations can be easily visually. Additionally, post imaging processing techniques, including the application of specific electronic image filter systems, can be employed to further amplify the color gradient contrast and make the heating pattern and cold spot locations more easily-identifiable.

Referring now to FIG. 1, a schematic perspective view of a packaged model food composition 100 for use in thermal testing is shown in accordance with various embodiments herein. A model food composition 104 is shown disposed within a package 102. The model food composition can include a model food material and an irreversible thermochromic ink. As used herein, "irreversible thermochromic ink" refers to a heat-sensitive permanent color change ink that does not reverse to its original color upon cooling. Model food materials, irreversible thermochromic inks, and thermal testing processes will be discussed in more detail below.

Irreversible thermochromic inks suitable for use herein can include those that exhibit a variable change in more than one color parameter in response to temperature change across a selected temperature range. In some embodiments, the color parameters include the three Commission Internationale de L'Éclairage (CIE) (L*, a*, and b*) color dimensions, as will be discussed more fully below.

The model food composition can include 0.05 weight % (wt. %) to 20 wt. % irreversible thermochromic ink. In some embodiments, the model food composition can include 0.1 wt. % to 10 wt. % irreversible thermochromic ink. In some embodiments, the model food composition can include at least 0.05 wt. %, 0.1 wt. %, 0.5 wt. %, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, or 25 wt. % of an irreversible thermochromic ink. It will be appreciated that the wt. % of the thermochromic ink in the model food composition can fall within a range wherein any of the forgoing percentages can serve as the lower or upper bound of the range, provided that the lower bound of the range is a value less than the upper bound of the range.

The model food composition can include a model food material that shares processing characteristics with a target food material. Desirable processing characteristics shared between the model food material and target food material can include, but are not limited to, thermal conductivity, specific heat, moisture content, dielectric constant, dielectric loss factor, penetration depth, and salt concentration. In addition, the packaged model food composition can be the same shape and size as a similarly packaged target food material. Though the packaged model food composition shown in FIG. 1 has a rectangular shape, it will be appreciated that the packaged model food composition can assume many configurations, including but not limited to a circle, a square, a hexagon, a cylinder, a cube, and an amorphous food packet, pouch, or sachet, and the like.

In some embodiments, the thermal testing of packaged model food composition 100 can be performed using a thermal process such as an electromagnetic wave-based thermal process.

Methods for Detecting Heating Patterns in Model Food Compositions

Figure 2:
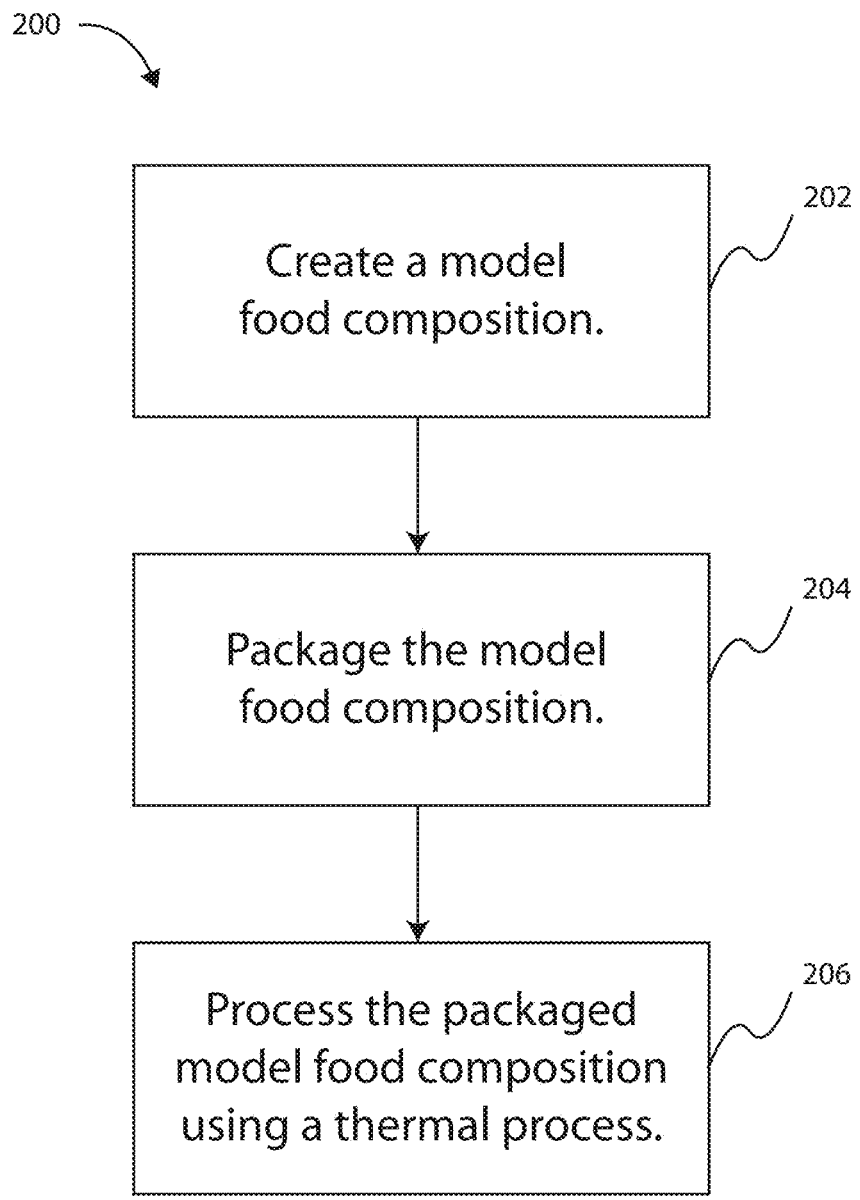
FIG. 2 is a flow chart of a method in accordance with various embodiments herein.
Figure 3:
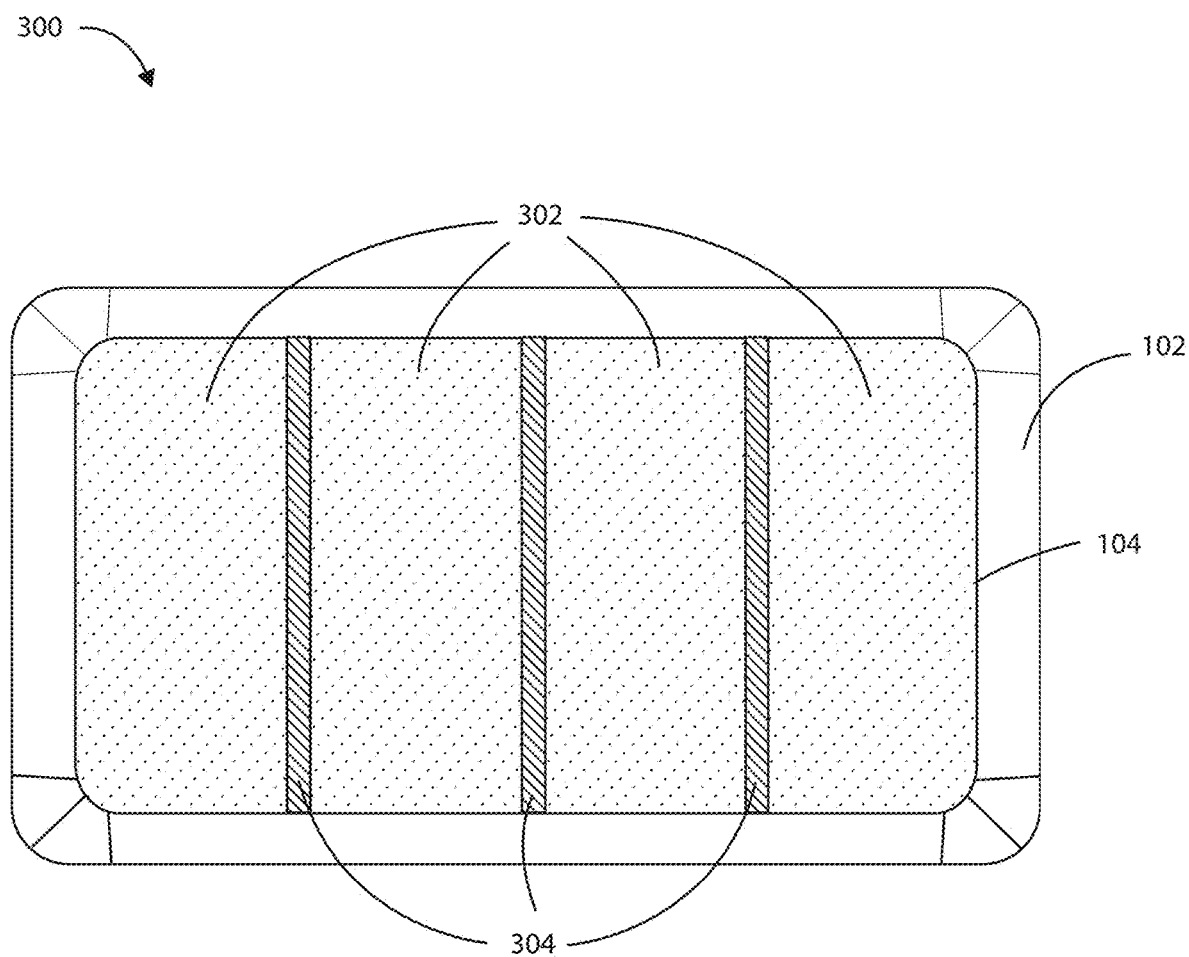
FIG. 3 is a schematic representation of a packaged model food composition in accordance with various embodiments herein.

The packaged model food compositions described herein are useful for detecting heating patterns during a thermal process. Referring now to FIG. 2, a flow chart of a method 200 for processing a model food composition is shown. The method 200 includes creating a model food composition by mixing a model food material and 0.05 wt. % to 20 wt. % of one or more irreversible thermochromic inks at 202. In some embodiments, only a single thermochromic ink is used. In other embodiments, two, three, four, five or more different thermochromic inks are used. As discussed elsewhere herein, the irreversible thermochromic ink is one that exhibits a variable change in more than one color parameter in response to temperature change across a selected temperature range. The method 200 includes packaging the model food composition by filling a food processing container with the model food composition and sealing the food processing container at 204. The method 200 includes processing the packaged model food composition in a thermal process at 206. Exemplary thermal processes, such as electromagnetic wave-based thermal processes, are discussed more fully below.

The step of processing the packaged model food composition in a thermal process can include exposing the packaged model food composition to one or more temperatures within a selected temperature range suitable for use with the thermal processes described herein. In some embodiments, the method 200 can include recording more than one change in a color parameter of the irreversible thermochromic ink in response to a change in temperature.

The method 200 can include transporting the packaged model food composition along a conveyor system within a thermal processing apparatus to a portion of the thermal processing apparatus that includes one or more microwave generating devices, such as a magnetron. A magnetron can generate electromagnetic radiation in the microwave wavelengths that can be used to heat food products. In some embodiments, the packaged model food composition can be transported along a conveyor system within a thermal processing apparatus to a location that includes one microwave generating device that is larger than the food processing container that contains the model food composition. In some embodiments, the packaged model food composition can be transported along a conveyor system within a thermal processing apparatus to a location that has one microwave generating device that is the same size as the food processing container that contains the model food composition.

In other embodiments, the packaged model food composition can be transported along a conveyor system within a thermal processing apparatus to a location, or locations, that include a plurality of microwave generating devices, placed either side-by-side or in series. The plurality of microwave generating devices can each irradiate at least a portion of a packaged model food composition for a predetermined amount of time. In some embodiments, the plurality of microwave generating devices can each irradiate the packaged model food composition simultaneously, while in other embodiments the plurality of microwave generating devices can each irradiate the packaged model food composition non-simultaneously.

For purposes of analysis, a packaged model food composition that is processed using electromagnetic wave generating devices can be divided into a plurality of target zones of electromagnetic radiation. The zones can also include a plurality of transition zones between neighboring target zones. In some embodiments, target zones and transition zones can experience a predetermined amount of heating, such as a targeted amount of heating. In some embodiments herein, methods can include identifying target zones based on previously known hot or cold spots within a given packaged model food composition.

By way of example, a schematic representation of a packaged model food composition 300 that has been treated using a thermal process with an electromagnetic wave based processing apparatus. The four target zones 302 within the packaged model food composition can each correspond to portions of relevance in the package such as zones containing cold spots, hot spots, or the like. The three transition zones 304 are disposed between adjacent target zones 302. When a model food composition experiences more than a targeted amount of electromagnetic radiation at a target zone or a transition zone, an irreversible thermochromic ink can report excessive heating in those areas. Similarly, if a transition zone does not experience electromagnetic radiation at a transition zone, an irreversible thermochromic ink can report a cold spot at the transition zone(s).

Figure 4:
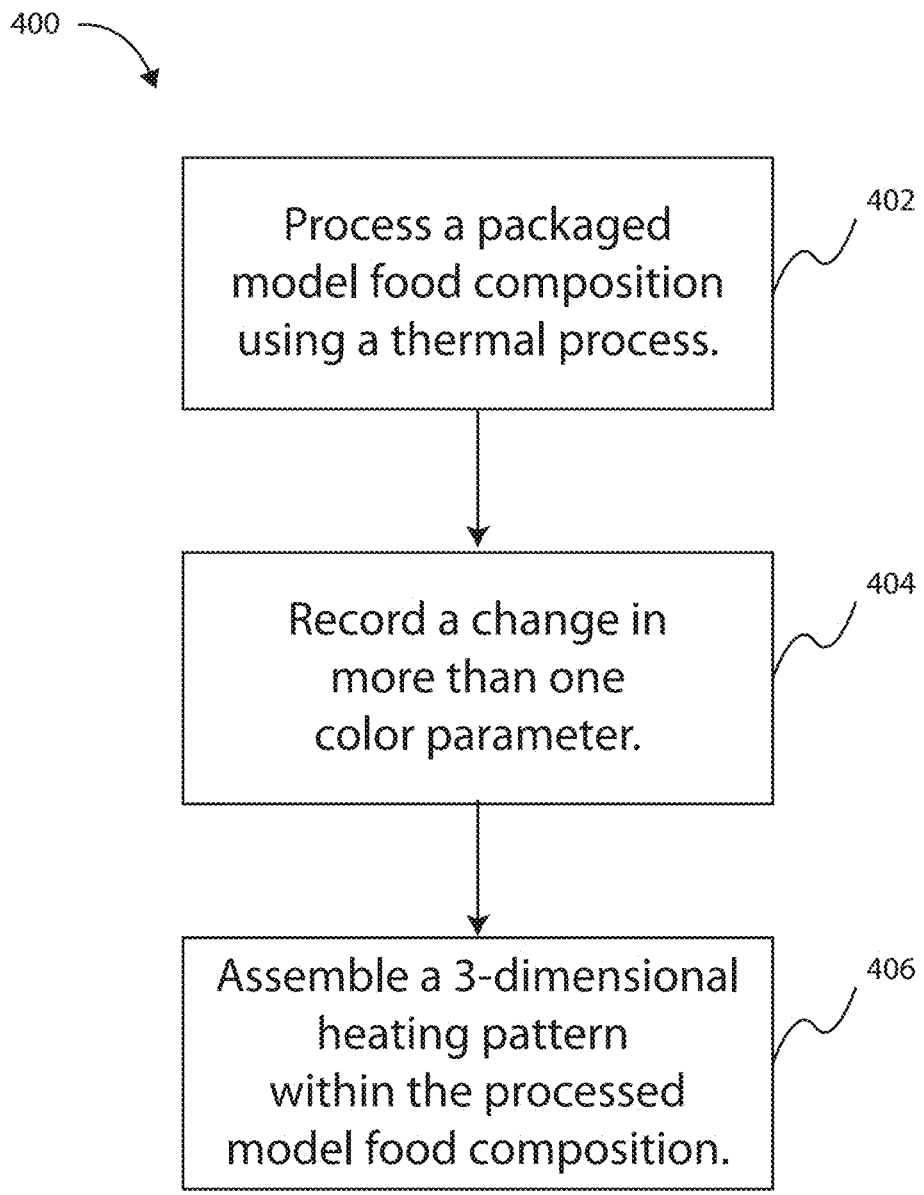
FIG. 4 is a flow chart of a method in accordance with various embodiments herein.

The packaged model food compositions described herein can be used in methods for detecting heating patterns within the model food composition. Referring now to FIG. 4, a flow chart of a method 400 for processing a packaged model food composition is shown. The method 400 includes processing the packaged model food composition using a thermal process across a selected temperature range at 402. The model food composition can include a model food material and 0.05 wt. % to 20 wt. % of an irreversible thermochromic ink. As discussed elsewhere herein, the irreversible thermochromic ink is one that exhibits a change in one, or more than one, color parameter in response to temperature change across a selected temperature range.

The method 400 can include recording more than one change in a color parameter of the irreversible thermochromic ink within the processed model food composition at 404. The method 400 can include using the change in one or more color parameters to assemble a 3-dimentional heating pattern within the processed model food composition at 406. The change in a color parameter at a unique location of the processed model food composition can indicate heat exposure (and/or the degree of heat exposure) within a particular location, and no change in a color parameter at a location of the processed model food composition can indicate the absence of heat exposure (and/or the degree of the absence of heat exposure) in that location. In some embodiments, the processed model food composition can be allowed to cool to room temperature prior to recording more than one change in a color parameter of the irreversible thermochromic ink.

Figure 5:
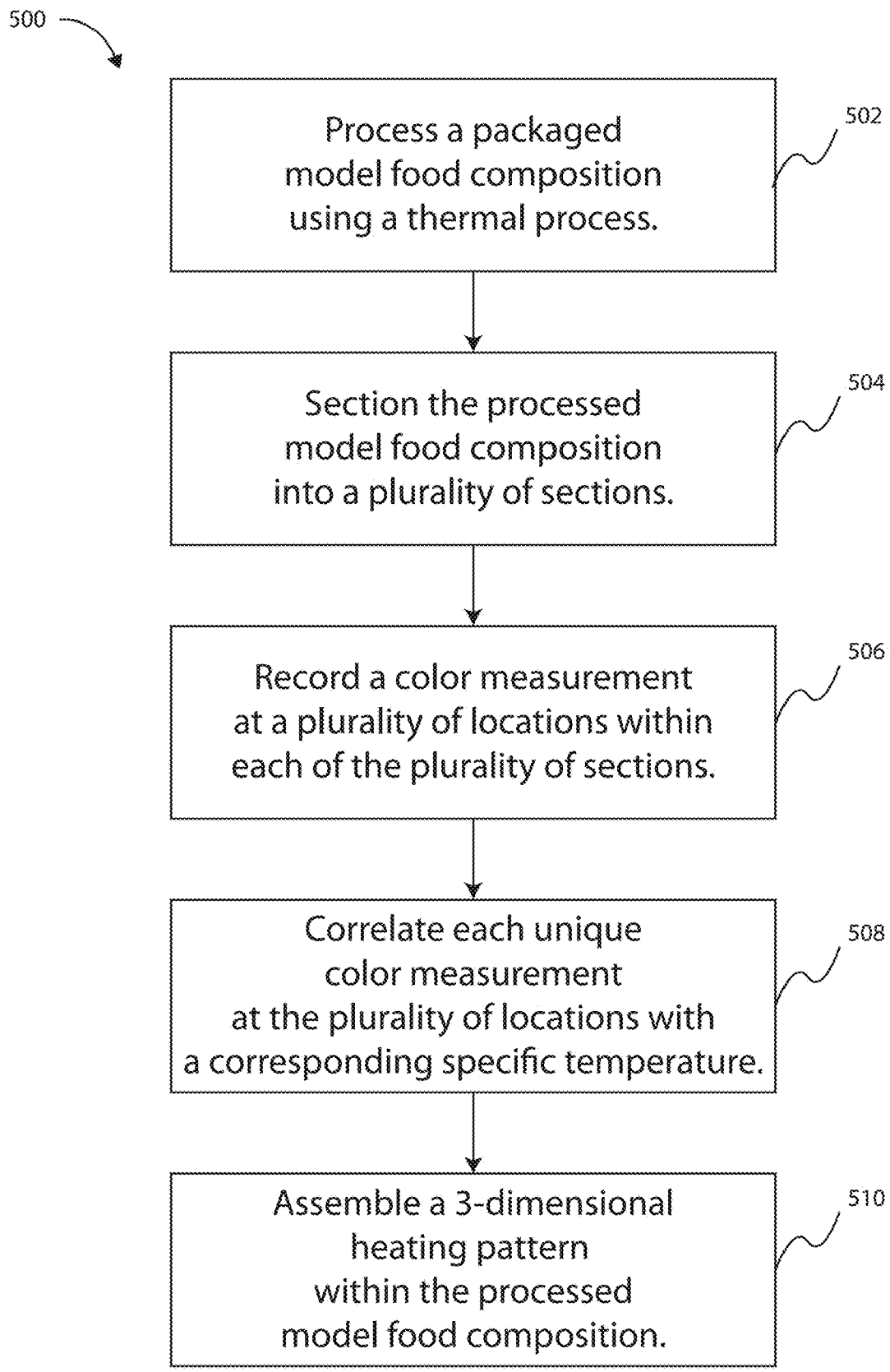
FIG. 5 is a flow chart of a method in accordance with various embodiments herein.

The packaged model food compositions described herein can also be used in methods for creating high-resolution temperature distribution profiles within the model food composition. Referring now to FIG. 5, a flow chart of a method 500 for detecting a high-resolution temperature distribution within a packaged model food composition is shown. The method 500 includes processing a packaged model food composition using a thermal process across a selected temperature range at 502. The model food composition can include a model food material and 0.05 wt. % to 20 wt. % of an irreversible thermochromic ink. As discussed elsewhere herein, the irreversible thermochromic ink is one that exhibits a variable change in more than one color parameter in response to temperature change across a selected temperature range.

The method 500 can include sectioning the processed model food composition into a plurality of sections, each in an X direction, a Y direction, and/or a Z direction at 504. In some embodiments, it will be appreciated that the model food composition can be removed from the food container prior to sectioning. In other embodiments, the food composition can be sectioned while still contained within the food container. In some embodiments, the model food composition can be preserved using a fixation process prior to sectioning, provided that the fixation process does not disrupt the color change within the model food composition. In some embodiments, the model food composition can be frozen prior to sectioning. The plurality of sections can then be examined with an imaging device, such as a spectrophotometer, high-resolution digital camera, or other piece of equipment. In various embodiments, the color measurement techniques, methods and/or devices used to measure temperature attainment when examining sections are the same as and/or are consistent with the color measurement techniques, methods and/or devices used to establish a color table and/or color curve. This approach can enhance the accuracy of the measurement technique.

The method 500 can include recording images at a plurality of locations within each of the plurality of sections using an imaging device. The images can be used to obtain a color measurement containing a change in one or more color parameters unique to each of the plurality of locations at 506. The unique color measurements obtained through imaging of each of the plurality of sections at a plurality of locations can be correlated to a corresponding specific temperature using a standard temperature color curve at 508. Once the images are recorded and translated to a corresponding temperature, the data can be assembled into a 3-dimentional temperature distribution profile within the processed model food composition at 510. In some embodiments, the method can further include post-image processing of each of the recorded color measurements and/or images using one or more electronic filter systems.

Sectioning of the packaged model food composition after a thermal processing step can include generating slices of the model food composition in any one or more of the x direction, a y direction, or a z direction. It will be appreciated that the size of the packaged model food composition can vary. By way of example, a rectangular-shaped model food composition, such as that shown in FIG. 1, can have the dimensions where the overall size is from about 10 to 400 mm in the x direction, by 10 to 300 mm in the y direction, by 10 to 300 mm in the z direction. Sectioning of such an exemplary rectangular-shaped model food composition can create sections having various dimensions. As just one example, for a block of L144 mm×W96 mm×D30 mm, if it is sliced in the depth direction D and each slice is 10 mm thick, if a typical reflected-color measurement device with 6 mm view/measurement field (e.g., HunterLab ColorFlex EZ or MiniScan EZ series equipment with selected nose cone adapter) is used, it is possible to get a mesh with 1152 points (three layers and each layer has 24×16 points) and each point with a specific temperature measurement. This greatly surpasses the measurement density of any conventional methods known. The 1152 color measurements can be used to assemble a mesh of a high-resolution, three-dimensional temperature distribution profile within the processed model food composition. In some embodiments, at least about 400, 500, 600, 700, 800, 900, 1000, 1100, 1200, 1300, 1400, 1500, 1600, 1700, 1800, 2000, 2200, 2400, 2600, 2800, or 3000 measurement points are used. In some embodiments, the number of measurement points can fall within a range between any of the foregoing.

Model Food Material

The model food material suitable for use herein can include one that has a color that provides for ease of measuring a change in the color parameters of the irreversible thermochromic ink in response to a change in temperature. In some embodiments, the model food material is a white color. In some embodiments, the model food material is a clear color. In addition, the model food material can be physically and chemically stable within the selected temperature range and selected duration of a thermal process, such that there is no change in its intrinsic color. For example, the model food material does not undergo a chemical reaction whereby the model food material itself changes color due to a change in temperature.

It will be appreciated that the Maillard reaction occurs between amino acids and reducing sugars and generates a brown color change. In specific embodiments herein, the model food material does not undergo any significant amount of Maillard reactions to turn from an initial color to a brown color in response to a change in temperature. In some embodiments, the model food material includes a very limited amount of amino acids and/or reducing sugars, or none at all thus reducing or eliminating the possible Maillard reactions that could take place. In some embodiments, the model food composition includes less than about 1.0, 0.7, 0.5, 0.3, 0.1, 0.05, 0.01, or 0.001 amino acid content by weight (including both free amino acids and those polymerized in the form of polypeptides). In some embodiments, the model food composition can include an amount of amino acids falling within a range between any of the foregoing amounts.

Suitable model food materials can include those having a white or clear color. Some examples of model food materials can include, but not be limited to, mashed white potatoes, mashed yellow potatoes, gellan gum, gelatin, agar, cellulose, methylcellulose, and the like.

The model food material can include one that has a viscosity that allows for the model food to be sectioned into one or more sections following a thermal process. In some embodiments, the viscosity of the model food material at 20° C. is at least 10,000 centipoise (cP). In some embodiments, the viscosity of the model food material at 20° C. is at least 50,000 cP. In some embodiments, the viscosity of the model food material at 20° C. is at least 500,000 cP. In some embodiments, the viscosity of the model food material at 20°

C. is 10,000 cP, 25,000 cP, 50,000 cP, 75,000 cP, 100,000 cP, 125,000 cP, 150,000 cP, 175,000 cP, 200,000 cP, 225,000 cP, 250,000 cP, 275,000 cP, 300,000 cP, 325,000 cP, 350,000 cP, 375,000 cP, 400,000 cP, 425,000 cP, 450,000 cP, 475,000 cP, 500,000 cP, 600,000 cP, 700,000 cP, 800,000 cP, 900,000 cP, 1,000,000 cP, 5,000,000 cP, or 10,000,000 cP. It will be appreciated that viscosity of the model food material at 20° C. can fall within a range wherein any of the forgoing viscosities can serve as the lower or upper bound of the range, provided that the lower bound of the range is a value less than the upper bound of the range. In some embodiments, it will be appreciated that addition of an irreversible thermochromic ink to a model food material, to form a model food composition, will not appreciably change the viscosity of the model food material.

Irreversible Thermochromic Inks/CIE L*a*b*Parameters

An irreversible thermochromic ink is a heat-sensitive, permanent color change ink that does not reverse to its original color upon cooling. Irreversible thermochromic inks can come in a variety of colors, where each ink has its own unique activation temperature at which the color transitions from an initial color to a final color. A suitable irreversible thermochromic ink can be chosen such that the color of the irreversible thermochromic ink in its ground state can change to a certain color at a temperature close to the lower end of a temperature range of a targeted thermal process. As used herein, the term "ink" shall also include thermochromic concentrates, dyes, and pigments, unless the context dictates otherwise.

In various embodiments, the activation temperature of the selected irreversible thermochromic inks can be about 40°, 42.5°, 45°, 47.5°, 50°, 52.5°, 55°, 57.5°, 60°, 62.5°, 65°, 67.5°, 70°, 72.5°, 75°, 77.5°, 80°, 82.5°, 85°, 87.5°, or 90° degrees Celsius. In some embodiments, the activation temperature of the selected irreversible thermochromic ink can fall within a range between any of the foregoing temperatures.

In some embodiments the irreversible thermochromic ink is one that transitions from a white color in its ground state to a magenta color in response to a temperature change. In some embodiments, the irreversible thermochromic ink is one that transitions from a white color in its ground state to a black color in response to a temperature change. In yet other embodiments, the irreversible thermochromic ink is one that transitions from a white color to any one of a turquoise, orange, or blue color in response to a temperature change. It will be appreciated that as an irreversible thermochromic ink transitions from an initial white to a final color, such as, for example, magenta, black, turquoise, orange, or blue color, the color density and optical density of the irreversible thermochromic ink will increase as temperature increases. In some embodiments, the color density and optical density increases monotonically in response to a temperature increase. In various embodiments herein, the color change of the irreversible thermochromic ink is not significantly impacted based on the amount of time that the ink is held at a particular temperature. As such, in various embodiments, the inks used herein are only sensitive to the temperature reached and not significantly affected by the amount of time they are held at a particular temperature.

As discussed above, irreversible thermochromic inks suitable for use herein can include those that exhibit a variable change in more than one color parameter in response to temperature change across a selected temperature range. Further, each temperature across a range of temperatures corresponds to a unique color and thus a unique set of color parameters for the irreversible thermochromic ink. For example, each unique color, and thus each unique set of color parameters, correspond to a unique CIE (L*, a*, b*) value set at each temperature. In some embodiments, the color parameters are those that are defined by the three Commission Internationale de L' Eclairage (CIE) color dimensions (L*, a*, and b*). The CIE L*a*b* is a three-dimensional model for describing the colors available to the human eye. The CIE L*a*b* model provides color profiles that are absolute values, and as such, is a device independent color space. The CIE L* color dimension represents lightness, where the blackest of black is represented by L*=0 and the brightest of white is represented by L*=100. The CIE a*color dimension represents the green-red color dimension, where the a axis extends from green (−a) to red (+a). The CIE b* color dimension represents the blue-yellow color dimension, where the b axis extends from the blue (−b) to red (+b).

In various embodiments herein, the irreversible thermochromic inks are not affected by processing variables in the thermal process other than the temperature, including but not limited to, mechanical stresses, pH changes, pressure variation, UV exposure, and hydration levels. In various embodiments herein, the irreversible thermochromic inks change by less than 5, 3, or 1% in terms of CIE L*a*b* parameter values as a result of mechanical stresses, pH changes, pressure variation, UV exposure, and hydration levels.

In various embodiments herein, the irreversible thermochromic inks are readily dispersible in a model food composition. As such, in various embodiments the thermochromic inks are dispersible in a food composition including a significant moisture content (e.g., a composition with an aqueous solvent and/or mixture with an aqueous continuous phase). In various embodiments, the irreversible thermochromic inks are formulated as an aqueous mixture (e.g., include an aqueous solvent).

In various embodiments herein, the irreversible thermochromic inks can be selected for a particular model food composition such that physical and chemical properties of the model food composition are not substantially changed by the addition of the irreversible thermochromic inks. For example, the irreversible thermochromic inks can be selected such that dielectric properties of the model food composition are not substantially changed by the addition of the irreversible thermochromic inks. In some embodiments, the dielectric properties of the model food composition, as measured at 915 Mhz, are changed by less than 30, 20, 10, 7.5, 5, 2.5, or 1 percent by the addition of the irreversible thermochromic inks.

In various embodiments herein, the irreversible thermochromic inks are not food grade. In various embodiments herein, the irreversible thermochromic inks are not edible. In various embodiments herein, the irreversible thermochromic inks are synthetic and not naturally occurring in food items.

In some embodiments, only a single irreversible thermochromic ink can be used. In other embodiments, multiple irreversible thermochromic inks can be used. In some embodiments, 1, 2, 3, 4, 5, 6, 7, or 8 irreversible thermochromic inks can be used. In some embodiments, the specific irreversible thermochromic inks selected can have different sensitive temperature ranges such that temperatures can be accurately measured across a range that is larger than the sensitive temperature range of any individual irreversible thermochromic ink used. As a specific example, in some embodiments, a combination of irreversible thermochromic inks can be chosen so that the resulting product can exhibit continuous color change from 20, 30, 40, 50, or 60 degrees Celsius up to 80, 90, 100, 110, 120, 130, 140 or 150 degrees Celsius.

In various embodiments, when multiple irreversible thermochromic inks are used, the specific irreversible thermochromic inks are selected so as to not be hindered or affected by the presence of the other irreversible thermochromic inks used. In various embodiments, when multiple irreversible thermochromic inks are used, the specific irreversible thermochromic inks are selected such that the interference between them is stable and repeatable so that this interference can be characterized and captured in the color table/curve development process.

In various embodiments, when multiple irreversible thermochromic inks are used, there is a unique set of CIE L*a*b* values corresponding to each and every specific temperature point within the temperature range of interest for each ink. As an example, for Ink I1, at temperature T1, it has color (L*I1T1, a* I1T1, b*I1T1), for Ink I2, at temperature T1, it has color (L*I2T1, a* I2T1, b* I2T1), for Ink In, at temperature Tn, it has color (L*InTn, a* InTn, b* InTn). In various embodiments, the specific inks are selected so that starting with ink I1 and then adding I2~ In, the color-temperature correspondence of I1 is not altered. In other words, for Ink I1, at temperature T1, we still have a unique (L*I1T1, a*I1T1, b*I1T1). The same can be true for inks I2~ In in the mixture. Thus, at any given temperature point Tx, the color of the mixture can be described also with a unique set of CIE L*a*b* values, (L*Tx, a*Tx, b*Tx) that equals to the superposition of all the colors of the component inks. In some embodiments, if there is interference between the inks, the addition of I2~ In at the certain concentration level results in for Ink I1, at temperature T1, results in (L*I1T1-1, a*I1T1-1, b*I1T1-1) instead of instead of having (L*I1T1, a* I1T1, b*T1). However, such a degree of interference still works, so long as the change(s) are stable and repeatable, meaning that for the given mixing ratios of I1 . . . n, and mixing and reaction conditions, this change is the same at this given temperature, and therefore resulting in a (different, yet) unique (and repeatable) set of CIEL*a*b* values, (L*Tx-1, a*Tx-1, b*Tx-1).

In various embodiments, when multiple irreversible thermochromic inks are used, the inks are selected such that the developed colors (e.g., the color the ink changes to as a result of exposure to a particular temperature) are not complementary colors of each other such that the colors changes don't cancel each other out.

In various embodiments, when multiple irreversible thermochromic inks are used, the amounts used of each irreversible thermochromic ink can be approximately equal. In other embodiments, when multiple irreversible thermochromic inks are used, the amounts used of each irreversible thermochromic ink can be different.

In various embodiments herein, the irreversible thermochromic inks can include one or more pigments/dyes. In various embodiments, the irreversible thermochromic inks can be dissolved in a solvent. In various embodiments, the irreversible thermochromic inks can be encapsulated and/or dispersed in a liquid carrier system. In some embodiments, the carrier system can include a solvent and, in some cases, other functional additives including, but not limited to, surfactants, dispersing agents, and other filler particles.

Many different specific irreversible thermochromic inks are contemplated herein. Exemplary irreversible thermochromic inks can include, but are not limited to, Kromagen W B Flexo Ink concentrate Magenta K60-NH TI21027 from LCR Hallcrest (Glenview, Ill.); Kromagen Black K115-NH from LCR Hallcrest (Glenview, Ill.); Kromagen W B Flexo Ink concentrate Turquoise K60-NH from LCR Hallcrest (Glenview, Ill.).

Thermal Food Processing Techniques

Thermal food processing techniques suitable for use when thermal testing a packaged model food composition can include, but not be limited to, microwave and/or radiofrequency based thermal processes.

Electromagnetic wave based thermal processing is a process of heating a packaged food product using microwave electromagnetic radiation for a predetermined amount of time and at a predetermined temperature or range of temperatures to reduce or eliminate pathogenic microorganisms from a packaged food product. These techniques can preserve the freshness of a packaged food product while prolonging its shelf life.

Electromagnetic wave energy can include energy at various frequencies. For example, electromagnetic wave energy can be applied at a frequency from approximately 300 MHz to approximately 2550 MHz or between 800 MHz to approximately 2550 MHz. In some embodiments, electromagnetic wave energy can be applied at a frequency of about 915 MHz or about 2450 Mhz. In some embodiments, electromagnetic wave energy can be applied at a frequency of about 13.56 MHz to 300 MHz.

In some cases a process of sterilizing a packaged food product using high pressure for a predetermined amount of time and at a predetermined temperature or range of temperatures to eliminate pathogenic microorganisms from a packaged food product can also be used. In these approaches, high pressures, ranging from 400-1200 megapascal (MPa) can be combined with the elevated temperatures described herein. In some embodiments, the processing can be performed at high pressures ranging from 500-1000 mPa. In some embodiments, the processing can be performed at high pressures ranging from 700-900 mPa.

The thermal processes described herein can be performed at a temperature from 20° C. to 150° C. In some embodiments, the thermal processes described herein can be performed at a temperature from 10° C. to 250° C. In some embodiments, the thermal processes described herein can be performed at a temperature from 30° C. to 100° C. In some embodiments, the thermal process can be performed at 10° C., 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., or 250° C. It will be appreciated that thermal process can be performed at a temperature that can fall within a range wherein any of the forgoing temperatures can serve as the lower or upper bound of the range, provided that the lower bound of the range is a value less than the upper bound of the range.

Aspects may be better understood with reference to the following examples. These examples are intended to be representative of specific embodiments, but are not intended as limiting the overall scope of embodiments herein.

EXAMPLES

Example 1

Creating a Standard Color Table/Curve Using a Magenta Irreversible Thermochromic Ink A model food material was mixed with a magenta irreversible thermochromic ink at a concentration of 10 wt. % to create a model food composition. Twenty ml of the model food composition was placed into 5 clean 50 ml beakers. The model food material was mashed potatoes. The irreversible thermochromic ink was creamy white prior to activation and specifically designed for low temperature activation.

Figure 6:
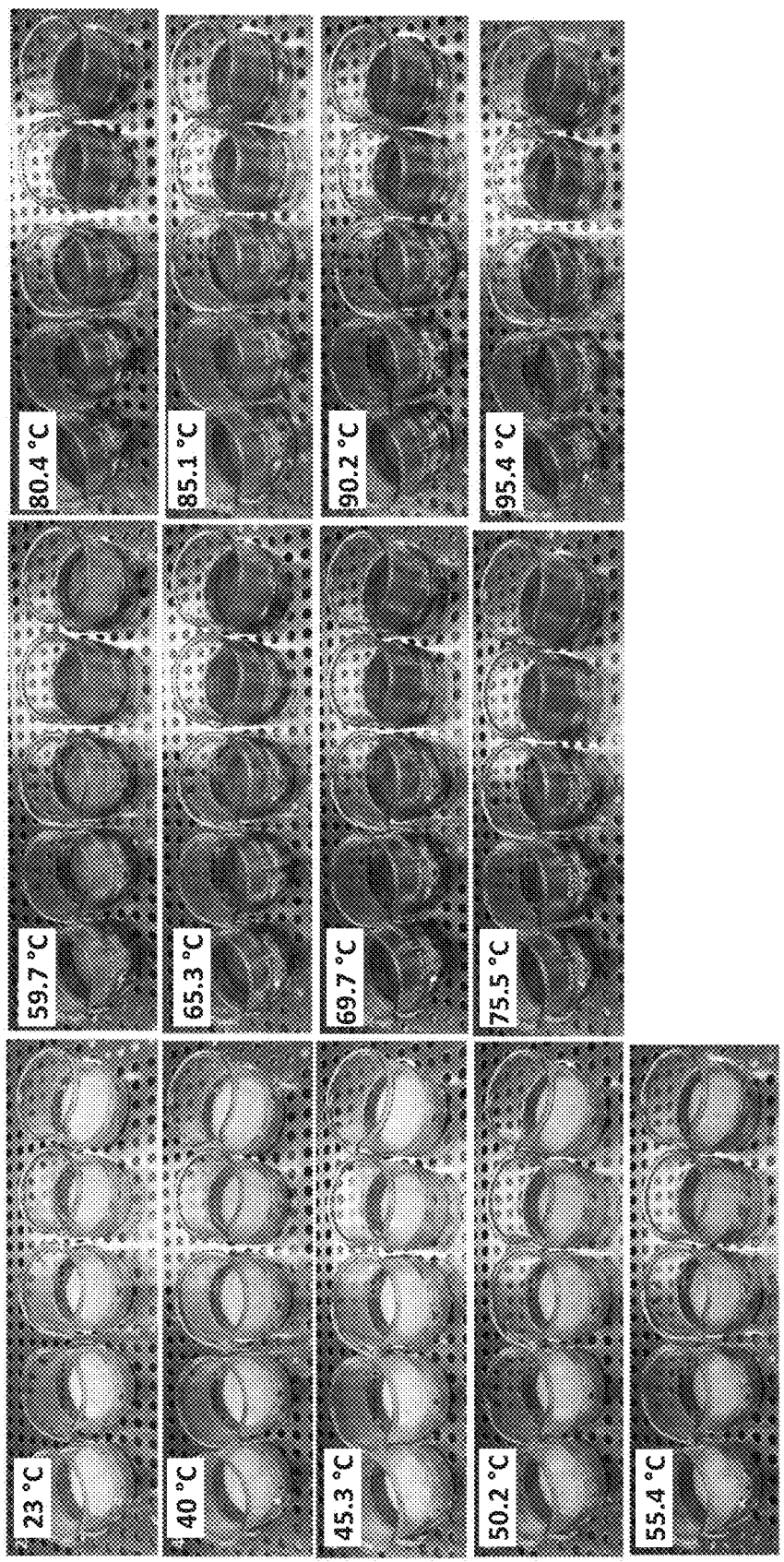
FIG. 6 is a series of color photographs of thermochromic ink at various temperatures in accordance with various embodiments herein.

A ThermoScientific Precision Reciprocal Shaking Bath was set to 40° C. To ensure the correct reading of the temperature of the water bath, an additional thermal couple (in addition to a hand-held thermometer) was placed into the water bath. Once the set temperature of 40° C. was reached, the 5×50 ml beakers containing the model food composition were placed onto the shelf in the center of the water bath in such a way that the water level slightly exceeded the sample fill line in the small beakers, as shown in FIG. 6. The beakers were heated in the water bath for 10 minutes to bring the temperature of the model food composition to 40° C. The beakers were then taken out and wiped clean and let to sit out at room temperature for 10 minutes to cool. Each beaker was individually placed onto a Hunterlab ColorFlex EZ spectrophotometer to determine the CIE L*a*b* color measurement at an illuminant/observer combination of D65/10° for each beaker at that specific temperature.

The water bath temperatures were raised from 40° C. up to 100° C. at an approximate 5° C. increment. The same set of 5×50 ml samples were placed back into the water bath and heated, sequentially, to each target temperature within the temperature range of 40° C. to 95° C. in a controlled manner (e.g., heated in a water/oil bath with precise temperature control). At each temperature increment, the above-mentioned color measurements were repeated. Specifically, color measurements were recorded when the model food compositions reached 40° C., 45.3° C., 50.2° C., 55.4° C., 59.7° C., 65.3° C., 69.7° C., 75.5° C., 80.4° C., 85.1° C., 90.2° C., and 95.4° C. While FIG. 6 is shown in grayscale, it illustrates a change from a white color to a deep magenta color with increasing temperature. A control color measurement was also recorded at a room temperature of 23° C. The raw data values, averages, and standard error of the mean (+/−SEM) are presented in TABLE 1 below.

TABLE 1

| CIE L*a*b* Values for Magenta Irreversible Thermochromic Ink Measured at Different Temperatures | | | | | | | | | | | | |
|---|---|---|---|---|---|---|---|---|---|---|---|---|
| Temperature | Sample 1 | | | Sample 2 | | | Sample 3 | | | Sample 4 | | |
| (° C.) | L* | a* | b* | L* | a* | b* | L* | a* | b* | L* | a* | b* |
| 23 | 88.98 | 1.83 | 7.99 | 88.08 | 1.88 | 8.29 | 88.71 | 2.13 | 8.38 | 87.8 | 1.98 | 8.07 |
| 40 | 88.36 | 2.71 | 7.43 | 87.23 | 2.74 | 7.64 | 88.24 | 2.7 | 7.88 | 87.14 | 2.92 | 7.41 |
| 45.3 | 87.09 | 4.83 | 6.11 | 85.99 | 4.75 | 6.29 | 87.27 | 4.37 | 6.73 | 85.85 | 5.04 | 5.97 |
| 50.2 | 84.15 | 10.08 | 2.61 | 83 | 10.24 | 2.65 | 83.96 | 10.36 | 2.8 | 83.14 | 9.85 | 2.77 |
| 55.4 | 68.64 | 35.4 | −13.34 | 70.69 | 30.31 | −10.53 | 75.72 | 24.41 | −6.49 | 72.09 | 28.27 | −9.15 |
| 59.7 | 48.5 | 54.1 | −21.65 | 48.48 | 52.78 | −21.26 | 52.19 | 51.94 | −21.25 | 49.56 | 52.49 | −21 |
| 65.3 | 41.51 | 54.3 | −20.55 | 40.84 | 53.79 | −20.22 | 42.64 | 54.56 | −20.61 | 41.75 | 54.16 | −20.12 |
| 69.7 | 38.78 | 53.85 | −19.99 | 37.81 | 53.16 | −19.36 | 39.57 | 53.88 | −19.9 | 38.81 | 53.58 | −19.45 |
| 75.5 | 35.33 | 52.47 | −18.91 | 34.53 | 51.93 | −18.28 | 36.33 | 52.76 | −18.98 | 35.53 | 52.45 | −18.37 |
| 80.4 | 33.57 | 51.39 | −18.17 | 33.56 | 51.41 | −18.06 | 33.33 | 50.88 | −17.65 | 31.6 | 50.61 | −16.42 |
| 85.1 | 36.18 | 52.57 | −19.53 | 35.98 | 52.78 | −18.96 | 36.11 | 52.61 | −19.5 | 34.15 | 52.25 | −18.25 |
| 90.2 | 35.45 | 53.4 | −20.12 | 34.66 | 51.91 | −19.58 | 35.48 | 52.57 | −19.95 | 34.41 | 52.42 | −19.26 |
| 95.4 | 38.74 | 53.77 | −20.02 | 37.59 | 52.53 | −20.09 | 38.35 | 53.33 | −20.69 | 35.99 | 53.92 | −18.84 |

| Temperature | Sample 5 | | | Sample Averages | | | SEM (+/−) | | |
|---|---|---|---|---|---|---|---|---|---|
| (° C.) | L* | a* | b* | L* | a* | b* | L* | a* | b* |
| 23 | 87.64 | 1.71 | 8.07 | 88.24 | 1.91 | 8.16 | 0.26 | 0.07 | 0.07 |
| 40 | 87.01 | 2.58 | 7.51 | 87.60 | 2.73 | 7.57 | 0.29 | 0.05 | 0.09 |
| 45.3 | 85.91 | 4.48 | 6.26 | 86.42 | 4.69 | 6.27 | 0.31 | 0.12 | 0.13 |
| 50.2 | 82.99 | 9.72 | 2.82 | 83.45 | 10.05 | 2.73 | 0.15 | 0.12 | 0.04 |
| 55.4 | 72.99 | 26.76 | −8.17 | 72.03 | 29.03 | −9.54 | 1.18 | 1.86 | 1.16 |
| 59.7 | 50.18 | 52.32 | −21.07 | 49.78 | 52.73 | −21.25 | 0.68 | 0.37 | 0.11 |
| 65.3 | 41.42 | 54.18 | −20.01 | 41.63 | 54.20 | −20.30 | 0.29 | 0.12 | 0.12 |
| 69.7 | 38.64 | 53.4 | −19.37 | 38.72 | 53.57 | −19.61 | 0.28 | 0.14 | 0.14 |
| 75.5 | 35.11 | 52.22 | −18.16 | 35.37 | 52.37 | −18.54 | 0.29 | 0.14 | 0.17 |
| 80.4 | 32.6 | 50.73 | −17.08 | 32.93 | 51.00 | −17.48 | 0.38 | 0.17 | 0.33 |
| 85.1 | 35.55 | 52.7 | −18.88 | 35.59 | 52.58 | −19.02 | 0.38 | 0.09 | 0.24 |
| 90.2 | 36.43 | 53.27 | −19.53 | 35.29 | 52.71 | −19.69 | 0.36 | 0.28 | 0.15 |
| 95.4 | 35.85 | 53.89 | −18.91 | 37.30 | 53.49 | −19.71 | 0.59 | 0.26 | 0.36 |

Figure 7:
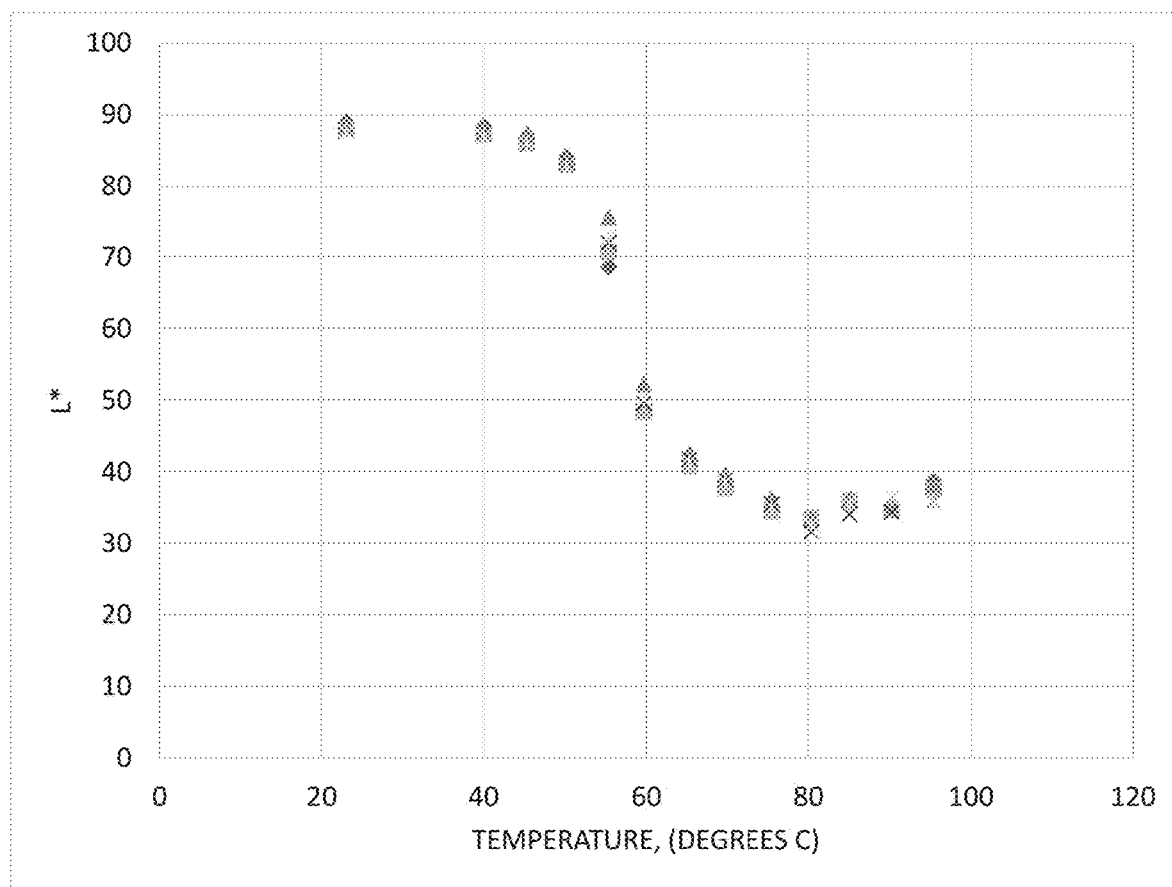
FIG. 7 is a plot of lightness (L*) versus temperature (° C.) in accordance with various embodiments herein.
Figure 8:
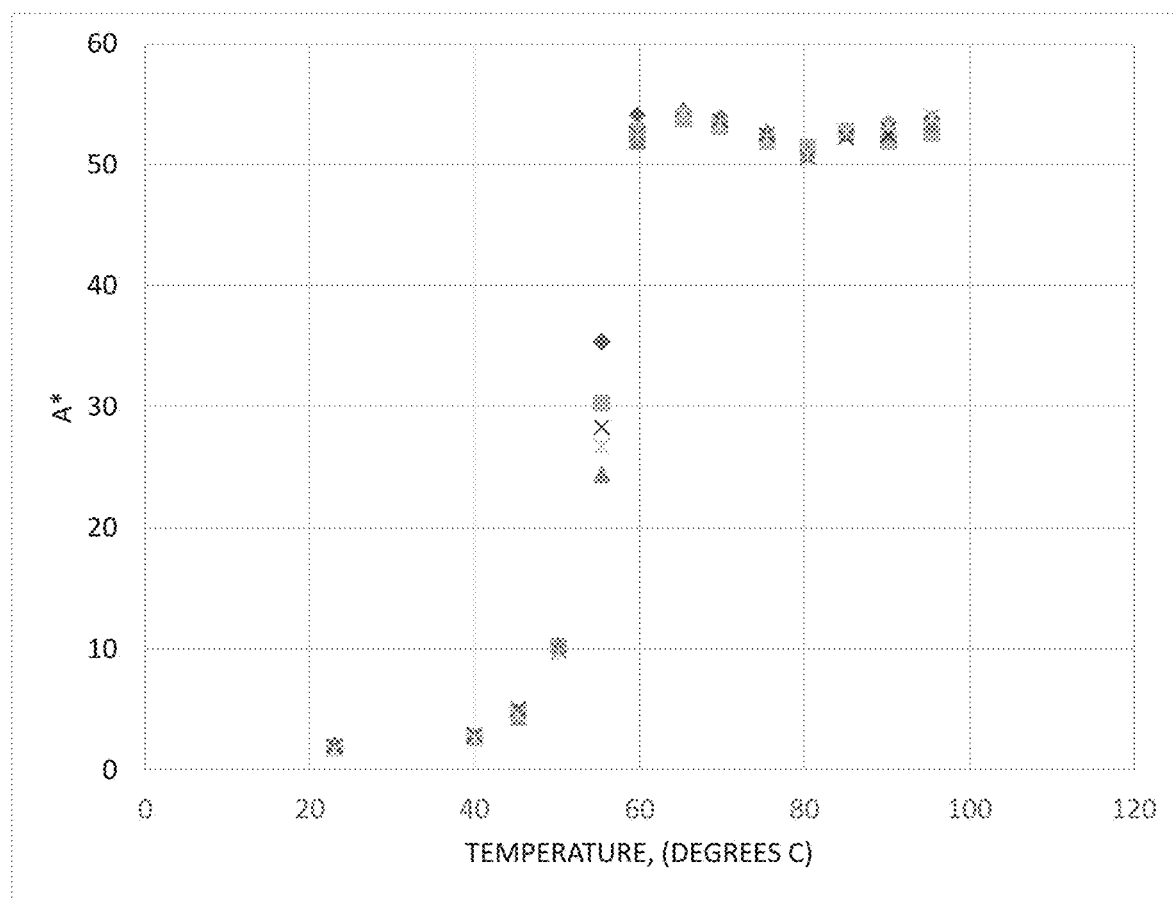
FIG. 8 is a plot of the CIE color dimension a* (redness/greenness) versus temperature (° C.) in accordance with various embodiments herein.
Figure 9:
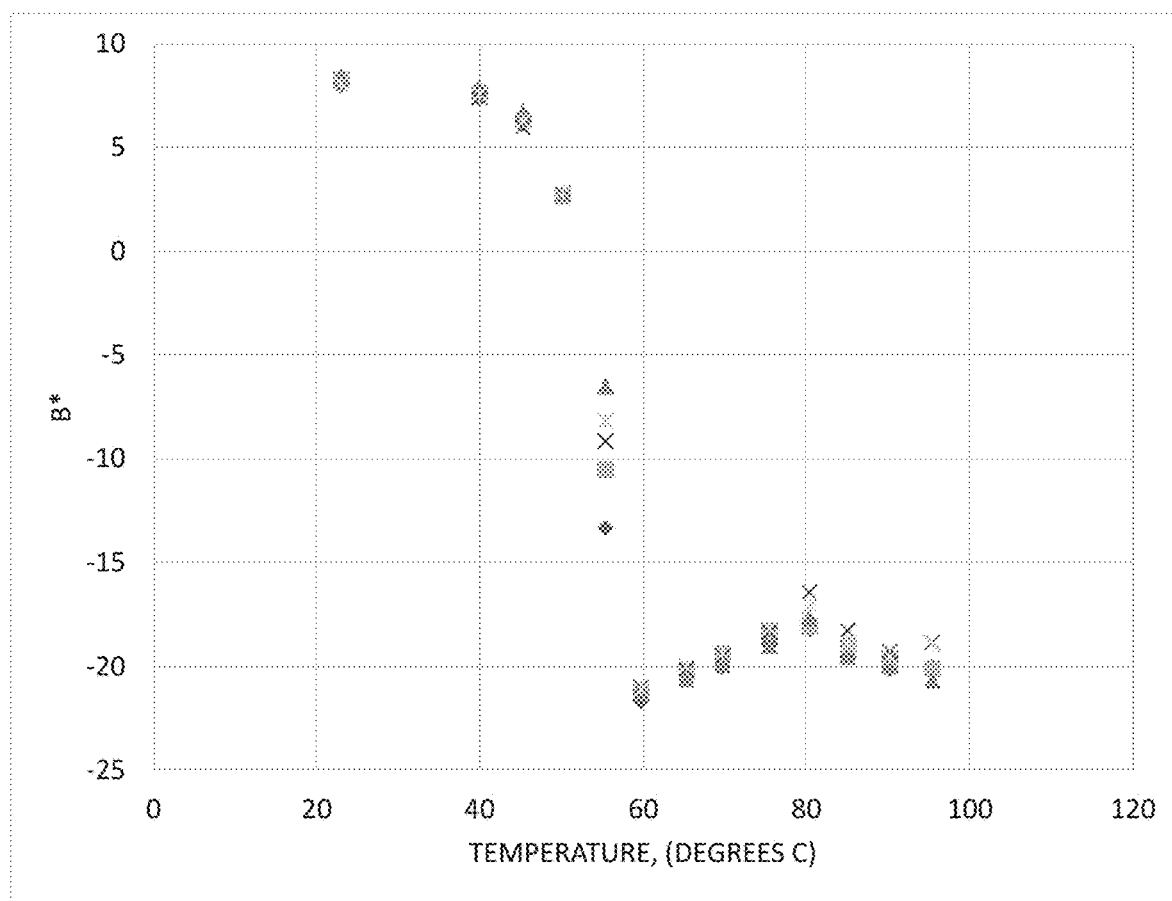
FIG. 9 is a plot of the CIE color dimension b* (yellowness/blueness) versus temperature (° C.) in accordance with various embodiments herein.

Color photographs for the samples at each temperature stop are shown in FIG. 6. Plots containing CIE L*a*b* color measurements as a function of temperature in ° C. are shown in FIGS. 7-9. FIG. 7 shows a standard curve for CIE lightness (L*) as a function of temperature (° C.). FIG. 8 shows a standard curve for the CIE a color dimension (a*) as a function of temperature (° C.). FIG. 9 shows a standard curve for the CIE b color dimension (b*) as a function of temperature (° C.).

The irreversible thermochromic ink used was a creamy white color prior to activation. Once thermally activated, the color changed irreversibly with the increased temperature. At approximately 45-50° C., the color change became detectable and the continued to develop as the temperature increased until it developed into full bright magenta color. The irreversible thermochromic ink exhibited its strongest color point at approximately 65° C. (See FIG. 8).

Example 2

Thermal Processing of a Mashed Potato Model Food Composition

Figure 10:
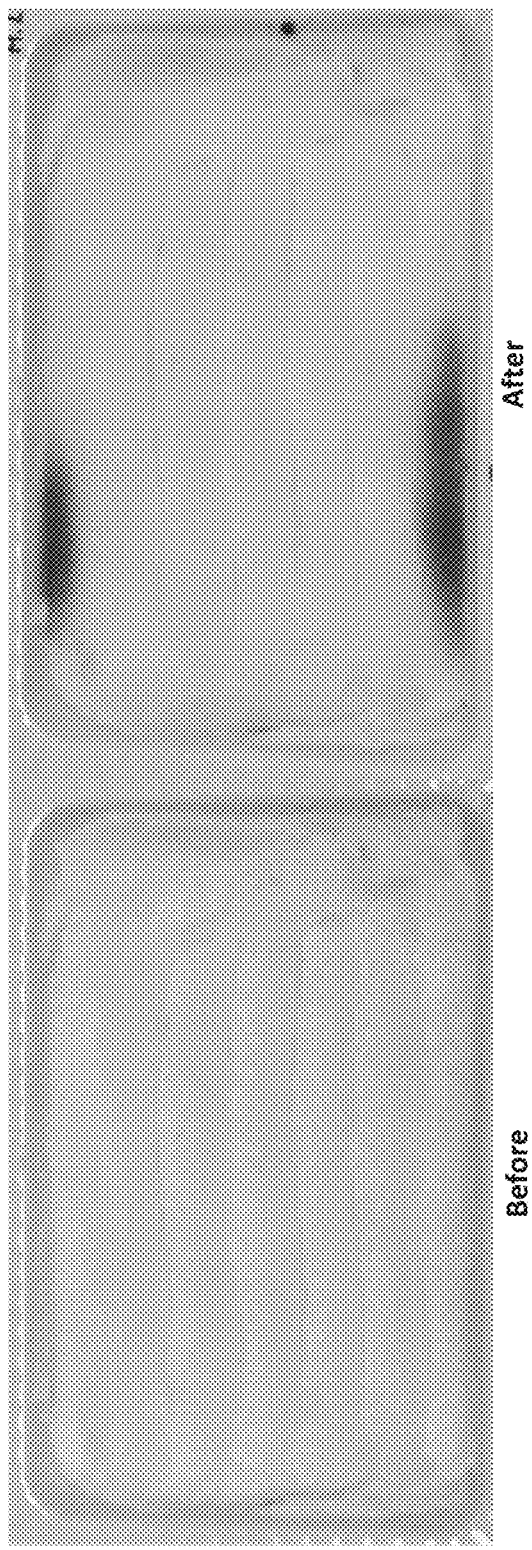
FIG. 10 is a set of photographs of a model food composition in accordance with various embodiments herein.
Figure 12:
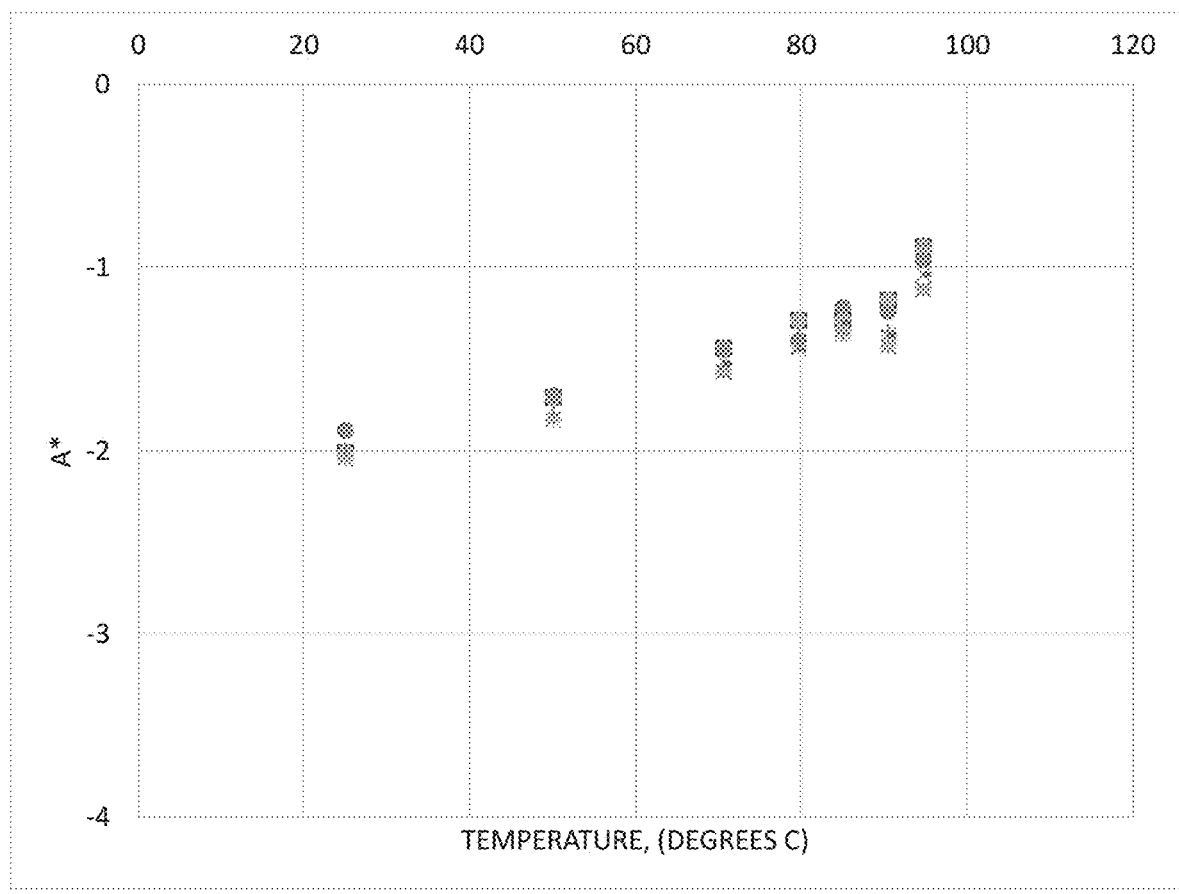
FIG. 12 is a plot of the CIE color dimension a* versus temperature (° C.) in accordance with various embodiments herein.
Figure 13:
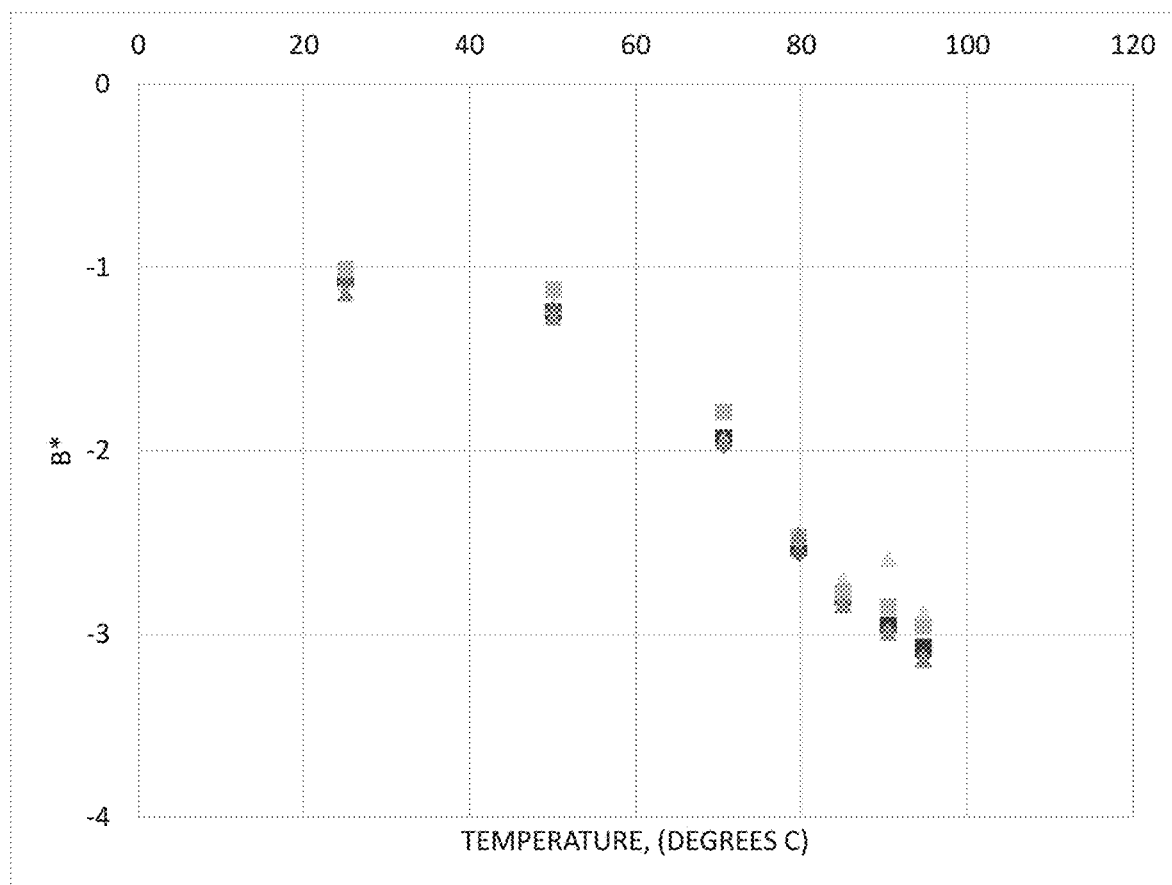
FIG. 13 is a plot of the CIE color dimension b* versus temperature (° C.) in accordance with various embodiments herein.

The mixture of Example 1 was filled into a food processing container and passed through a microwave heating process as discussed herein. The resultant thermal heating pattern is shown in FIG. 10 (shown in grayscale, but reflecting regions of magenta color in the after picture). The model food composition before the microwave heating process is shown on the left of FIG. 10 and the model food composition after the microwave heating process is shown on the right of FIG. 10. The irreversible thermochromic ink turned from a milky white to a magenta pink color upon heating. Regions within the model food composition that appear magenta are regions that were heated during the microwave heating process. Regions within the model food composition that are not magenta were not heated to the same levels as the regions where the color significantly changed towards magenta during the microwave heating process. The more heated the regions, the greater the optical density of the irreversible thermochromic ink (e.g., seen as a deep magenta color). The less heated the regions, the lower the optical density of the irreversible thermochromic ink (e.g., seen as a white or light pink color).

function of temperature (° C.). FIG. 12 shows a standard curve for the CIE a color dimension (a*) as a function of temperature (° C.). FIG. 13 shows a standard curve for the CIE b color dimension (b*) as a function of temperature (° C.).

TABLE 2

CIE L*a*b* Values for Black Irreversible Thermochromic Ink Measured at Different Temperatures

| Temperature | Sample 6 | | | Sample 7 | | | Sample 8 | | | Sample 9 | | |
|---|---|---|---|---|---|---|---|---|---|---|---|---|
| (° C.) | L* | a* | b* | L* | a* | b* | L* | a* | b* | L* | a* | b* |
| 25 | 79.37 | −2.01 | −1.06 | 79.29 | −2 | −1.08 | 79.71 | −2.04 | −1.08 | 78.83 | −2.04 | −1.01 |
| 50.1 | 79.95 | −1.71 | −1.24 | 79.02 | −1.8 | −1.21 | 79.41 | −18 | −1.23 | 78.73 | −1.83 | −1.12 |
| 70.6 | 73.58 | −1.44 | −1.93 | 73.63 | −1.54 | −1.94 | 74 | −1.52 | −1.97 | 74.02 | −1.57 | −1.79 |
| 79.7 | 68.79 | −1.29 | −2.54 | 69.11 | −1.37 | −2.54 | 69.24 | −1.44 | −2.56 | 68.64 | −1.43 | −2.47 |
| 85 | 66.04 | −1.29 | −2.8 | 66 | −1.36 | −2.7 | 66.84 | −1.3 | −2.83 | 65.89 | −1.34 | −2.77 |
| 90.5 | 64.41 | −1.18 | −2.95 | 63.19 | −1.35 | −2.59 | 64.44 | −1.37 | −2.98 | 63.88 | −1.43 | −2.85 |
| 94.7 | 62.41 | −0.89 | −3.07 | 62.84 | −0.88 | −2.88 | 63.05 | −1.04 | −3.12 | 62.71 | −1.12 | −2.96 |

| Temperature | Sample 10 | | | Sample Averages | | | SEM (+/−) | | |
|---|---|---|---|---|---|---|---|---|---|
| (° C.) | L* | a* | b* | L* | a* | b* | L* | a* | b* |
| 25 | 78.16 | −1.89 | −1.14 | 79.072 | −1.996 | −1.074 | 0.267739 | 0.027677 | 0.020881 |
| 50.1 | 77.75 | −1.7 | −1.27 | 78.972 | −5.008 | −1.214 | 0.367592 | 3.248097 | 0.025417 |
| 70.6 | 72.82 | −1.45 | −1.95 | 73.61 | −1.504 | −1.916 | 0.21744 | 0.025417 | 0.032187 |
| 79.7 | 68.9 | −1.4 | −2.46 | 68.936 | −1.386 | −2.514 | 0.107917 | 0.026944 | 0.020396 |
| 85 | 65.58 | −1.22 | −2.84 | 66.07 | −1.302 | −2.788 | 0.20871 | 0.024166 | 0.025179 |
| 90.5 | 63.45 | −1.24 | −2.99 | 63.874 | −1.314 | −2.872 | 0.250531 | 0.045453 | 0.074726 |
| 94.7 | 61.85 | −0.96 | −3.14 | 62.572 | −0.978 | −3.034 | 0.208192 | 0.045651 | 0.049558 |

Example 3

Creating a Standard Color Table/Curve Using a Black Irreversible Thermochromic Ink A model food material was mixed with a black irreversible thermochromic ink at a concentration of 5 wt. % to create a model food composition. The model food composition was filled into a food processing container. The model food material was gellan gum. The irreversible thermochromic ink was creamy white prior to activation and specifically designed for high temperature activation. Following the procedures similar to those presented in Example 1, a color table/color space curve was developed.

CIELAB color measurements for each temperature stop, including 25° C., 50.1° C., 70.6° C., 79.7° C., 85° C., 90.5° C., and 94.7° C. are shown in TABLE 2.

Figure 11:
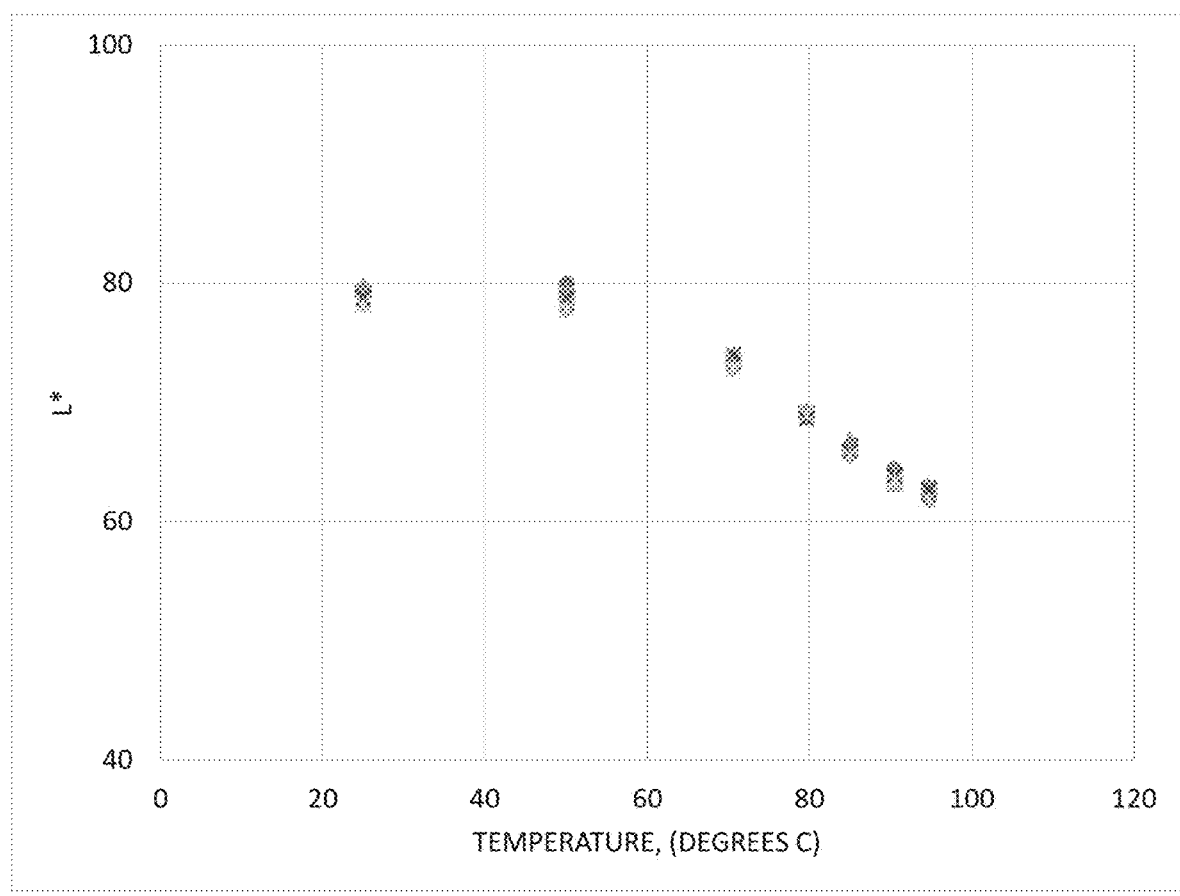
FIG. 11 is a plot of lightness (L*) versus temperature (° C.) in accordance with various embodiments herein.

Plots containing CIE L*a*b* color measurements as a function of temperature in ° C. are shown in FIGS. 11-13. FIG. 11 shows a standard curve for CIE lightness (L*) as a Example 4

Thermal Processing of a Gellan Gum Model Food Composition

The mixture of Example 3 was filled into a food processing container and passed through a microwave heating process. The resultant thermal heating pattern is shown in the photographs in FIGS. 14 and 15. The model food composition before the microwave heating process is shown on the top left (top of model food composition before heating) and top right (bottom of model food composition before heating) of FIG. 14. The model food composition after the microwave heating process is shown on the bottom left (top of model food composition after heating) and bottom right (bottom of model food composition after heating) of FIG. 14. The irreversible thermochromic ink turned from a milky white to a black color upon heating. Regions within the model food composition that appear black are regions that were heated during the microwave heating process. Regions within the model food composition that are not black were not heated during the microwave heating process.

Figure 14:
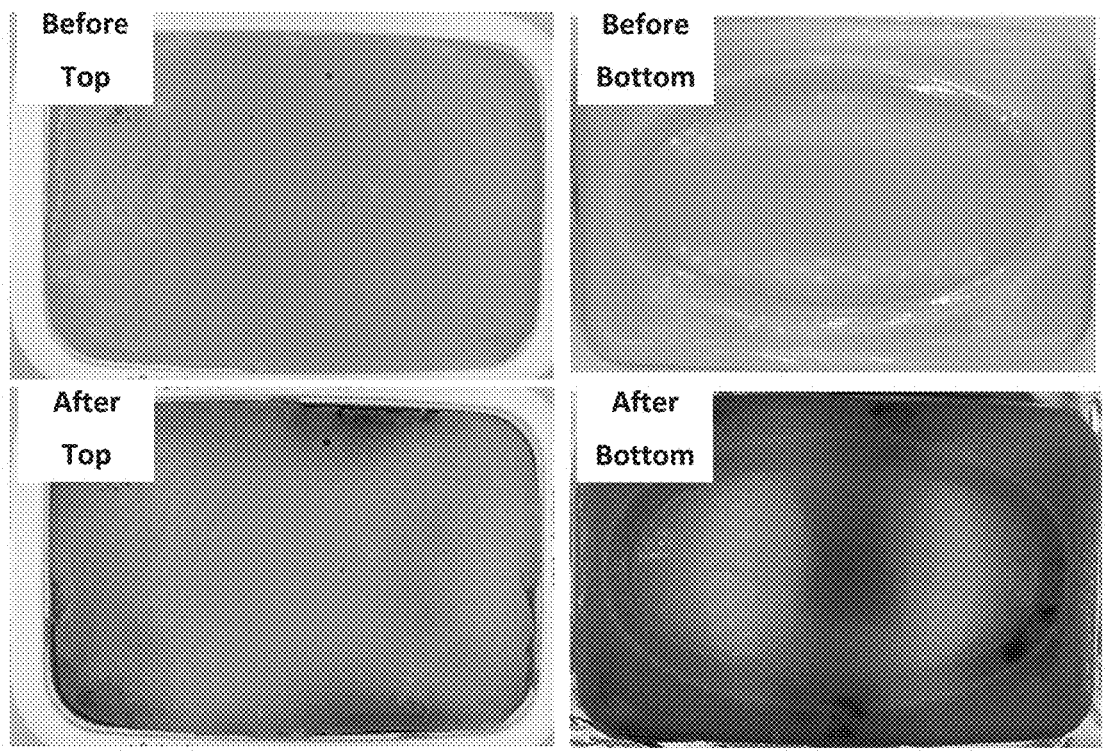
FIG. 14 is a set of photographs of a model food composition in accordance with various embodiments herein.
Figure 15:
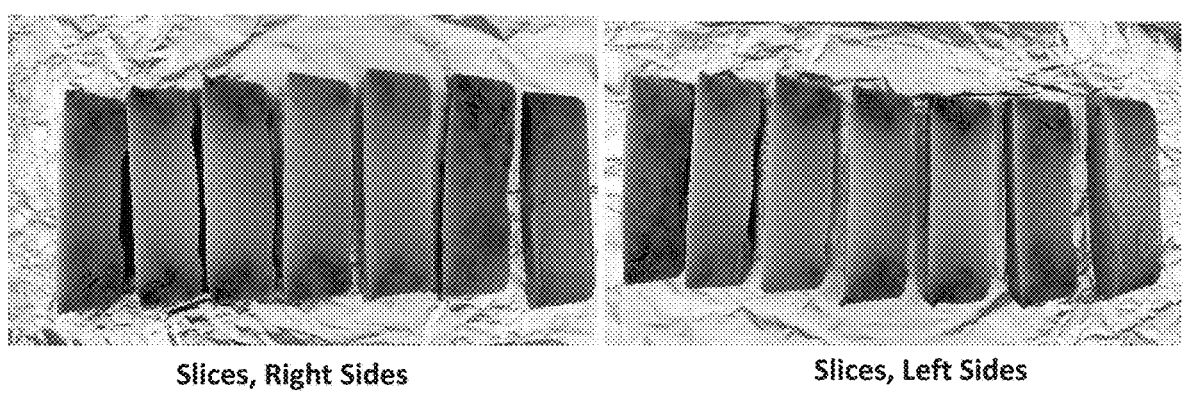
FIG. 15 is a set of photographs of a model food composition in accordance with various embodiments herein.

The model food composition shown in FIG. 14 had the dimensions of 144 mm in length by 96 mm in width by 30 mm in height. The model food composition was sectioned in the y direction into 7 individual sections of approximately 20 mm each, as shown in FIG. 15. Inspection of the left and right sides of each slide revealed an unevenly distributed heating pattern within the model food composition. The more heated the regions, the greater the optical density of the irreversible thermochromic ink (e.g., seen as a deep black color). The less heated the regions, the lower the optical density of the irreversible thermochromic ink (e.g., seen as a clear to opaque or light gray color).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of processing a packaged model food composition comprising:
   creating a model food composition by mixing a model food material and 0.05 wt. % to 20 wt. % of one or more irreversible thermochromic inks;
   wherein one or more irreversible thermochromic inks exhibit a variable change in more than one color parameter in response to temperature change across a selected temperature range;
   packaging the model food composition by filling a food processing container with the model food composition and sealing the food processing container; and
   processing the packaged model food composition in a thermal process.

2. The method of claim 1, the thermal process comprising an electromagnetic wave based thermal process.

3. The method of claim 1, wherein the thermal process includes heating the packaged model food composition to a temperature within a selected temperature range.

4. The method of claim 1, wherein the thermal process includes heating the packaged model food composition within a selected temperature range from 20 degrees C. to 150 degrees C.

5. The method of claim 1, wherein processing the packaged model food composition includes transporting the packaged model food composition along a conveyor to a microwave generating device that irradiates the packaged model food composition for a predetermined amount of time.

6. The method of claim 1, further comprising identifying and recording changes in at least one color parameter of the irreversible thermochromic ink.

7. The method of claim 1, further comprising identifying and recording changes in at least one color parameter of the irreversible thermochromic ink at 800 or more distinct locations within the packaged model food composition.

8. The method of claim 7, further comprising using the recorded changes to construct a three-dimensional temperature distribution profile of the packaged model food composition.

9. The method of claim 1, wherein mixing a model food material and 0.05 wt. % to 20 wt. % of an irreversible thermochromic ink results in a mixture that exhibits average dielectric properties that are less than 10 percent different than for the model food material by itself.

10. The method of claim 1, wherein the irreversible thermochromic ink is synthetic and inedible.

11. A method for detecting a heating pattern within a packaged model food composition comprising:
    processing a packaged model food composition using a thermal process across a selected temperature range, the model food composition comprising a model food material and 0.05 wt. % to 20 wt. % of one or more irreversible thermochromic inks;
    wherein the one or more irreversible thermochromic inks exhibit a variable change in more than one color parameter in response to temperature change across the selected temperature range;
    recording more than one change in a color parameter of the one or more irreversible thermochromic inks within the processed model food composition; and
    assembling a 3-dimentional heating pattern within the processed model food composition using the recorded color parameter changes.

12. The method of claim 11, wherein a change in a color parameter at a unique location of the processed model food composition indicates a heated location, and no change in a color parameter at a location of the processed model food composition indicates a non-heated location.

13. The method of claim 11, the color parameter comprising a CIE L*, CIE a*, or CIE b* color dimension.

14. The method of claim 11, wherein each temperature across the selected temperature range corresponds to a unique set of color parameters for the irreversible thermochromic ink, the unique set of color parameters comprising a unique CIE (L*, a*, b*) value set for each temperature.

15. A method for detecting a high-resolution temperature distribution within a packaged model food composition comprising:
    processing a packaged model food composition using a thermal process across a selected temperature range, the model food composition comprising a model food material and 0.05 wt. % to 20 wt. % of one or more irreversible thermochromic inks;
    wherein the one or more irreversible thermochromic inks exhibit a variable change in more than one color parameter in response to temperature change across the selected temperature range;
    sectioning the processed model food composition into a plurality of sections, each in an x direction, a y direction, or a z direction;
    recording images at a plurality of locations within each of the plurality of sections using an imaging device to obtain a color measurement containing one or more color parameters unique to each of the plurality of locations;
    assembling a 3-dimentional temperature distribution profile within the processed model food composition.

16. The method of claim 15, the color parameter comprising a CIE L*, CIE a*, or CIE b* color dimension.

17. The method of claim 15, wherein each temperature across the selected temperature range corresponds to a unique set of color parameters for the irreversible thermochromic ink, the unique set of color parameters comprising a unique CIE (L*, a*, b*) value set for each temperature.

18. The method of claim 15, wherein a color measurement is recorded in increments in the x direction and the y direction of each of the sections such that a three-dimensional mesh of at least 800 color measurements is recorded for the packaged model food composition.

19. The method of claim 18, wherein the color measurements are used to assemble a 3-dimentional temperature distribution profile within the processed model food composition.

20. The method of claim 15, the imaging device comprising a spectrophotometer or a high resolution digital camera.

* * * * *